United States Patent [19]

Semeraro et al.

[11] Patent Number: 4,935,548

[45] Date of Patent: * Jun. 19, 1990

[54] 1.4-DIHYDROPYRIDINES

[75] Inventors: Claudio Semeraro, Bresso; Dino Micheli, Carpi; Daniele Pieraccioli; Giovanni Gaviraghi, both of Verona, all of Italy; Alan D. Borthwick, London, United Kingdom

[73] Assignee: Glaxo S.p.A, Italy

[*] Notice: The portion of the term of this patent subsequent to Jan. 31, 2006 has been disclaimed.

[21] Appl. No.: 262,240

[22] Filed: Oct. 21, 1988

Related U.S. Application Data

[63] Continuation of Ser. No. 16,254, Feb. 19, 1987, abandoned.

[30] Foreign Application Priority Data

Feb. 20, 1986 [IT]  Italy ................. 19482 A/86

[51] Int. Cl.$^5$ ................. C07D 211/86; A61K 31/455
[52] U.S. Cl. ..................... 514/356; 514/344; 546/321; 546/286
[58] Field of Search .............. 546/321, 286; 514/356, 514/344

[56] References Cited

U.S. PATENT DOCUMENTS

| | | | |
|---|---|---|---|
| 3,923,818 | 12/1975 | Bossert et al. | 546/321 |
| 4,307,103 | 12/1981 | Sato et al. | 546/321 |
| 4,492,703 | 1/1985 | Goldmann et al. | 546/321 |
| 4,801,599 | 1/1989 | Semeraro et al. | 546/321 |
| 4,806,533 | 2/1989 | Semeraro et al. | 546/321 |

OTHER PUBLICATIONS

Rahwan, R. et al., Annual Reports in Medicinal Chemistry 16 (1981) pp. 257–268.

Thomas G. et al., J. Cardiovascular Pharm. 6, pp. 1170–1176 (1984).

Primary Examiner—Jane T. Fan

[57] ABSTRACT

Compounds are described of the formula

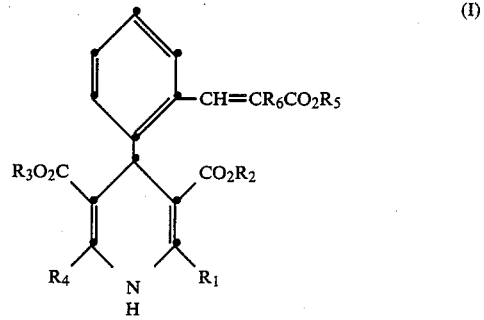

(I)

wherein $R_1$ represents a formyl or nitrile group or a group $OCH_2A$ where A represents hydroxy, $C_{1-4}$ alkoxy or $D(CH_2)_nNR_7R_8$ (where $R_7$ and $R_8$ independently represent hydrogen or $C_{1-4}$ alkyl and n is 2 or 3);

$R_2$ and $R_3$ independently represent a $C_{1-6}$ straight or branched alkyl chain or alkoxy group;

$R_4$ represents a $C_{1-4}$ alkyl group;

$R_5$ represents a straight or branched chain $C_{1-13}$ alkyl group or a $C_{5-8}$ cycloalkyl group which may be substituted by a $C_{1-3}$ alkyl substituent;

$R_6$ represents a halogen atom or a straight or branched $C_{1-3}$ alkyl group.

The compounds represented by formula (I) reduce intracellular calcium ion concentration by limiting transmembranal calcium ion influx and thus may be useful for the treatment of cardiovascular disorders such as hypertension.

19 Claims, No Drawings

1.4-DIHYDROPYRIDINES

This application is a continuation of Ser. No. 016,254, filed Feb. 19, 1987 now abandoned.

This invention relates to novel heterocyclic derivatives which have an effect on the transmembranal influx of calcium ions into the cells of cardiac and smooth muscle, to processes for the preparation thereof, to pharmaceutical compositions containing them and to their use in therapeutics.

The role of intracellular calcium ions in the control of the contractile system of cardiac and smooth muscle is well known. Furthermore it has been established that compounds which limit the intracellular calcium ion concentration by preventing or reducing the transmembranal calcium ion influx in cells of the contractile system of cardiac and smooth muscle are useful in the treatment of cardiovascular disorders.

We have now found a new group of compounds which reduce intracellular calcium ion concentration by limiting transmembranal calcium ion influx and thus may be useful for the treatment of cardiovascular disorders such as hypertension, angina pectoris, myocardial ischaemia, congestive heart failure, cerebral vascular and peripheral disorders, and for the treatment of diseases characterised by reversible airway obstruction such as asthma and chronic bronchitis.

The invention thus provides for compounds of the general formula (I).

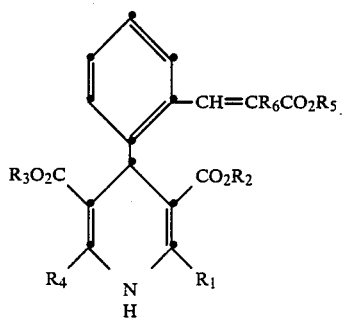

and physiologically acceptable salts thereof, in which
$R_1$ represents a formyl or nitrile group or a group $CH_2A$ where A represents hydroxy, $C_{1-4}$ alkoxy or $O(CH_2)_nNR_7R_8$ (where $R_7$ and $R_8$ independently represent hydrogen or $C_{1-4}$ alkyl and n is 2 or 3);
$R_2$ and $R_3$ independently represent a $C_{1-6}$ straight or branched chain alkyl or alkoxyalkyl group;
$R_4$ represents a $C_{1-4}$ alkyl group;
$R_5$ represents a $C_{1-3}$ alkyl group or a $C_{5-8}$ cycloalkyl group which may be substituted by a $C_{1-3}$ alkyl group; and
$R_6$ represents a hydrogen or halogen atom or a $C_{1-3}$ alkyl group.

The compounds represented by formula (I) can exist in more than one isomeric and/or enantiomeric form and the invention includes all such isomers, enantiomers and mixtures thereof.

The term 'alkyl' as a group or part of a group means that the group is straight or branched.

The compounds of formula (I) in which the group $R_1$ is basic forms salts with inorganic or organic acids. Particularly suitable salts are those of physiologically acceptable inorganic and organic acids and include hydrochlorides, hybrobromides, sulphates, p-toluene- sulphonates, methanesulphonates, formates, acetates, maleates, fumarates, succinates, phosphates, citrates, tartrates and benzoates.

Examples of suitable groups for $R_1$ include hydroxymethyl, $C_{1-2}$ alkoxymethyl (e.g. ethoxymethyl), formyl, nitrile, $CH_2OCH_2CH_2N(CH_3)_2$ and $CH_2OCH_2CH_2NH_2$.

Examples of suitable groups for $R_2$ and $R_3$ independently include $C_{1-4}$ alkyl groups such as methyl, ethyl, isopropyl, isobutyl, or t-butyl groups or a $C_{1-4}$ alkyl group (such as ethyl) substituted by $C_{1-3}$ alkoxy (e.g. methoxy or propoxy).

Examples of suitable group for $R_4$ include methyl and ethyl groups.

When the group $R_5$ represents a $C_{1-13}$ alkyl group this may for example be a methyl, ethyl, propyl, isopropyl, butyl, sec butyl, isobutyl, tert butyl, pentyl, isopentyl, neopentyl, hexyl, 2,6-dimethyl-4-heptyl, octyl or a tridecyl group. When $R_5$ represents a cycloalkyl group, conveniently this represents a cyclopentyl, cyclohexyl or cycloheptyl group, which may be substituted by a methyl group.

When $R_6$ represents a $C_{1-3}$ alkyl group this may for example be a methyl, ethyl or n-propyl group, and is preferably a methyl or ethyl group.

When $R_6$ represents a halogen atom this may for example by chlorine, bromine or iodine and is preferably bromine.

The group $-CH=CR_6CO_2R_5$ in the compounds of formula (I) can exist in the (Z) or the (E) configuration, and preferred compounds are those in which the hydrogen atom and the group $R_6$ are trans with respect to each other.

$R_1$ preferably represents hydroxymethyl, nitrile or $CH_2OCH_2CH_2N(CH_3)_2$.

$R_2$ and $R_3$ preferably independently represent $C_{1-4}$ alkyl for example a methyl and/or more preferably an ethyl group.

$R_4$ preferably represents a methyl group.

$R_5$ preferably represents a $C_{2-9}$ alkyl group, and is more preferably tert butyl.

$R_6$ preferably represent a methyl or ethyl group or more preferably a hydrogen atom.

Particularly preferred compound according to the invention are 2-[(2-Dimethylamino-1-ethoxy)methyl]-6-methyl-4-(2-(3-(1,1-dimethylethoxy)-3-oxo-1-propenyl)phenyl)-1,4-dihydro-3,5-pyridinedicarboxylic acid, diethyl ester; 2-Hydroxymethyl-6-methyl-4-(2-(3-(1,1-dimethylethoxy)-3-oxo-1-propenyl)phenyl)-1,4-dihydro-3,5-pyridinedicarboxylic acid, diethyl ester; 2-Cyano-6-methyl-4-(2-(3-(1,1-dimethylethoxy)-3-oxo-1-propenyl)phenyl)-1,4-dihydro-3,5-pyridinedicarboxylic acid, diethyl ester and more particularly the (E) isomers thereof, and their physiologically acceptable salts.

The ability of the compounds to limit or inhibit the effect of calcium ions on the tone of vascular smooth muscle may be determined using a depolarised rabbit ear artery prepared according to the method of Towart. R. et al Br. J. Pharmacol. 1982, 75, 1508.

The antihypertensive activity of the compounds of the invention was demonstrated by intravenous and/or oral administration of the compound to male spontaneously hypertensve rats.

The compounds of the invention are thus of interest in the treatment of hypertension and diseases characterised by reversible airways obstruction such as asthma and chronic bronchitis. They are also potentially useful for the treatment of other cardiovascular disorders including angina pectoris, myocardial ischaemia, congestive heart failure, cerebral vascular and peripheral disorders.

The compounds of formula (I) may be formulated in a conventional manner for use with one or more pharmaceutical carriers or excipients.

Thus a further aspect of the invention includes pharmaceutical compositions the compounds of formula (I) formulated for oral, sub lingual, transdermal, parenteral or rectal administration, or for administration by inhalation or insufflation.

For oral administration the pharmaceutical composition may take the form of for example tablets, which may be film or sugar coated, capsules, powders, granules, solutions including syrups, or suspensions prepared by conventional means with acceptable excipients. For sub lingual administration the composition may take the form of tablets or lozenges formulated in the conventional manner.

A proposed daily dosage of active compound of the invention for the treatment of man is in the range of 0.03 mg to 100 mg, which may conveniently be administered in one or more doses. The precise dose employed will depend on the age and condition of the patient as well as the route of administration.

For oral use the compounds of the invention are conveniently administered to the human patient at a dose in the range 0.3 to 100 mg per day. For parenteral use the compounds of the invention are conveniently administered at a dose in the range of 0.03-30 mg per day.

For administration by inhalation use the compounds of the invention are conveniently administered to the human patient at a dose in the range of 0.1 mg to 10 mg per day.

For oral use the compound is preferably administered twice or more particularly once a day.

Methods for preparing the compounds of formula (I) are described below and for the intermediate described below $R_1$–$R_8$ and n have the meanings defined above for compounds of formula (I) or are such groupings in a protected form unless otherwise stated.

Compounds of formula (I) in which $R_1$ represents a formyl group, a $C_{1-4}$ alkoxymethyl group or a group $CH_2O(CH_2)_nNR_7R_8$ may be prepared by reacting the $\alpha,\beta$-unsaturated ketone (II) (where $R_aR_bCH$ represents $R_1$ as defined above or a protected derivative thereof) with the aminoester (III) followed by removal of any protecting groups where necessary.

The reaction is conveniently carried out in a solvent such as an alkanol, e.g. ethanol or isopropanol and preferably with heating e.g. 40°–150° C.

When $R_1$ represents a formyl group the reaction is conveniently carried out using a protected derivative of formula (II) in which $R_aR_bCH$ represents an acetal e.g. $(CH_3O)_2CH$ followed by hydrolysis to remove the protecting group. The hydrolysis may be effected using an organic acid such as formic, oxalic, acetic or trifluoroacetic acid or p-toluenesulphonic acid. Suitable solvents for the hydrolysis include water, ketones (e.g. acetone), alcohols (e.g. methanol or ethanol) or amides (e.g. N,N-dimethylformamide) or halogenated hydrocarbons (e.g. methylene chloride).

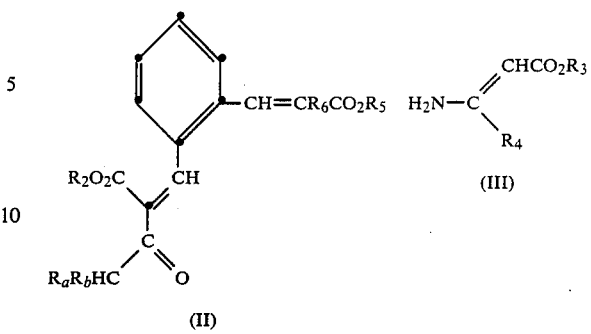

The $\alpha,\beta$-unsaturated ketone (II) may be prepared by reacting the aldehyde (IV) with the ketoester (V), in a solvent such as an alkanol e.g. ethanol or isopropanol or a hydrocarbon e.g. toluene, preferably with heating e.g. 40°–150° C. Conveniently this reaction is carried out in the presence of a catalyst such as piperidine or piperidine acetate.

In a modification of this process for preparing compounds of formula (I), the aldehyde (IV) may be reacted with a mixture of the aminoester (III) and the ketoester (V) in a solvent such as an alkanol e.g. ethanol or isopropanol or a hydrocarbon e.g. toluene or acetic acid, preferably with heating e.g. 40°–150° C.

Compounds of formula (I) in which $R_1$ has one meaning may be converted into compounds of formula (I) in which $R_1$ has another meaning using standard methods of interconversion.

Thus, compounds of formula (I) in which $R_1$ represents hydroxymethyl may be prepared from the corresponding formyl compound by reduction. Suitable reducing agents include alkali metal borohydrides such as sodium borohydride or sodium cyanoborohydride. The reaction takes place in the presence of a solvent such as an alcohol (e.g. ethanol) or an ether (e.g. tetrahydrofuran) or an amide (e.g. N,N-dimethylformamide).

Compounds of formula (I) in which $R_1$ represents a nitrile group may be prepared from the corresponding formyl compound by reaction with hydroxylamine or a salt thereof e.g. the hydrochloride followed by dehydration of the intermediate oxime. Reaction to form the oxime may conveniently be carried out under acidic conditions using for example acetic acid in the presence of an alkali metal acetate such as sodium acetate. Dehydration may be effected using a standard dehydrating agent such as a carboxylic acid anhydride e.g. acetic anhydride.

Compounds of formula (IV) may be prepared by reacting the bis aldehyde (VI) with the triphenylphosphorane (VII) in a solvent such as methylene chloride or toluene

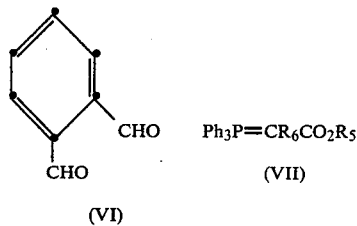

Compounds of formula (IV) may also be prepared by reacting the 2-halobenzaldehyde (VIII)

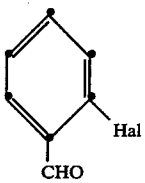

(where Hal represents a bromine or iodine atom) with an acrylic ester $CH_2=CR_6CO_2R_5$ (IX) in the presence of a catalytic amount of a palladium salt such as palladium acetate in the presence of a suitable organic base such as a trialkylamine e.g. triethylamine or tri-n-butylamine. The reaction is also preferably carried out in the presence of a triarylphosphine such as tri-o-tolyphosphine, or more preferably, triphenylphosphine.

The reaction is conveniently carried out in a suitable solvent such as xylene or t-butyl acetate, or more conveniently in dimethylformamide or in a mixture of solvents e.g. xylene/dimethylformamide, preferably with heating. The reaction mixture is preferably heated within the temperature range of 80° C. to 150° C., more preferably at 100° C. to 110° C.

The compounds of formulae (III), (V), (VI), (VII) and (VIII) are either known compounds or may be made by analogous methods to those used for known compounds.

The following examples illustrate the invention. Temperatures are in °C.

INTERMEDIATE 1

(E)-3-(2-Formylphenyl)-2-propenoic acid, 1,1-dimethyl ethyl ester

INTERMEDIATE 2

2-((E)-2-(3-(1,1-Dimethylethoxy)-3-oxo-1-propenyl)-phenyl)methylene-1-dimethoxy-3-oxo-butanoic acid, ethyl ester A solution of Intermediate 1 (33.7 g), 3-oxo-4,4-dimethoxybutanoic acid, ethyl ester (35.5 g) and piperidine (6.8 ml) in toluene (100 ml) was refluxed for 24 h separating water by azeotropic distillation. The mixture was extracted with ethyl acetate. After evaporation of the solvent the residue was purified by column chromatography on silica gel eluting with cyclohexane/ethyl acetate 7:3 to give the title compound (6 g) as an oil. T.l.c. (cyclohexane/ethyl acetate 6:4) Rf 0.43

INTERMEDIATE 3

2-(Dimethoxymethyl)-6-methyl-4(E)-(2-(3-(1,1-dimethylethoxy)-3-oxo-1-propenyl)phenyl)-1,4-dihydro-3,5-pyridinedicarboxylic acid, diethyl ester A solution of Intermediate 2 (12 g) and 3-amino-2-butenoic acid, ethyl ester (6.13 g) in ethanol (200 ml) was refluxed for 10 hours. After evaporation of the solvent, the residue was purified by column chromatography on silica gel eluting with cyclohexane/ethyl acetate 7:3 to give the title compound (5 g) as an oil.

EXAMPLE 1

2-[(2-Dimethylamino-1-ethoxy)methyl]-6-methyl-4(E)-(2-(3-(1,1-dimethylethoxy)-3-oxo-1-propenyl)phenyl)-1,4-dihydro-3,5-pyridinedicarboxylic acid, diethyl ester, hydrochloride A solution of 3-amino-4-(2-dimethylaminoethoxy)-2-butenoic acid, ethyl ester (24.11 g), Intermediate 1 (25.86 g), 3-oxobutanoic acid, ethyl ester (14.46 g) and acetic acid (0.5 ml) was refluxed for 18 h. After evaporation of the solvent, the residue was purified by column chromatography on silica gel eluting with 1,1,1-trichloroethane/methanol 9:2 to give the free base of the title compound (6 g). In a solution of free base (6 g) in ether was bubbled gaseous HCl to give the title compound as a white solid. M.p. 174°–715°.

Microanalysis for $C_{30}H_{42}N_2O_7 \cdot HCl$ requires: C62.21; H7.48; N4.83; Cl6.12; found: C60.48; H7.41; N4.77; Cl5.81%.

EXAMPLE 2

2-Formyl-6-methyl-4(E)-(2-(3-(1,1-dimethylethoxy)-3-oxo-1-propenyl)phenyl)-1,4-dihydro-3,5-pyridinedicarboxylic acid, diethyl ester A solution of Intermediate 3 (2.9 g), silica gel (10 g) and oxalic acid (0.7 g) in dichloromethane (35 ml) was stirring for 40 h at room temperature. After the evaporation of the solvent the residue was purified by column chromatography on silica gel eluting with cyclohexane/ethyl acetate 7:3 to give the title compound (1.5 g).

EXAMPLE 3

2-Hydroxymethyl-6-methyl-4-(E)-(2-(3-(1,1-dimethylethoxy)-3-oxo-1-propenyl)phenyl)-1,4-dihydro-3,5-pyridinedicarboxylic acid, diethyl ester A solution of the product of Example 2 (0.95 g) in ethanol (20 ml) was treated at 0° with sodium borohydride (0.76 g). The mixture was stirred for 30 min. and extracted with ethyl acetate. After evaporation of the solvent the residue was purified by column chromatography on silica gel eluting with cyclohexane/ethyl acetate 1:1 to give the title compound (0.2 g) as a white solid. M.p. 163°–164°. T.l.c. (cyclohexane/ethyl acetate 1:1) Rf 0.23.

EXAMPLE 4

2-Cyano-6-methyl-4(E)-(2-(3-(1,1-dimethylethoxy)-3-oxo-1-propenyl)-phenyl)-1,4-dihydro-3,5-pyridinedicarboxylic acid, diethyl ester A solution of the product of Example 2 (2.9 g), hydroxylamine hydrochloride (0.51 g) and sodium acetate (0.76 g) in acetic acid (30 ml) was stirred for 2 h at room temperature, then acetic anhydride (2.2 g) was added to the reaction. The mixture was heated to 95°–100° for 5 h and then extracted with ethyl acetate. The organic phase was washed with 5% sodium hydroxide and brine, dried over $Na_2SO_4$ and evaporated. The residue was purified by column chromatography on silica gel eluting with cyclohexane/ethyl acetate 7:3 to give the title compound (0.45 g) as a yellow solid. M.p. 146°–147°.

Microanalysis for: $C_{26}H_{30}N_2O_6$ Requires: C66.94; H6.48; N6.00; Found: C67.00; H6.45; N5.80%.

We claim:

1. A compound of the formula (I)

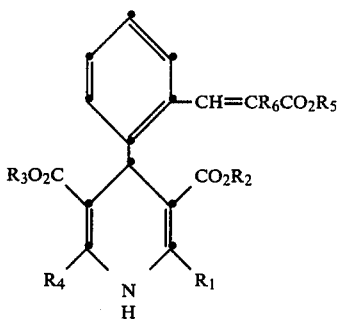

or a physiologically acceptable salt thereof, in which $R_1$ represents a formyl or nitrile group or a group $CH_2A$ where A represents hydroxy, $C_{1-4}$ alkoxy or $O(CH_2)_nNR_7R_8$ (where $R_7$ and $R_8$ independently represent hydrogen or $C_{1-4}$ alkyl and n is 2 or 3);

$R_2$ and $R_3$ independently represent a $C_{1-6}$ straight or branched chain alkyl or alkoxyalkyl group;

$R_4$ represents a $C_{1-4}$ alkyl group;

$R_5$ represents a $C_{1-13}$ alkyl group or a $C_{5-8}$ cycloalkyl group which may be substituted by a $C_{1-3}$ alkyl group; and $R_6$ represents a hydrogen or halogen atom or a $C_{1-3}$ alkyl group.

2. A compound as claimed in claim 1 in which $R_1$ represents hydroxymethyl, $C_{1-2}$ alkoxymethyl, formyl, nitrile, $CH_2OCH_2CH_2N(CH_3)_2$ or $CH_2OCH_2CH_2NH_2$.

3. A compound as claimed in claim 1 in which $R_1$ represents hydroxymethyl, nitrile or $CH_2OCH_2CH_2N(CH_3)_2$.

4. A compound as claimed in claim 1 in which $R_2$ and $R_3$ independently represent a methyl or ethyl group.

5. A compound as claimed in claim 1 in which $R_4$ represents a methyl group.

6. A compound as claimed in claim 1 in which $R_5$ represents a $C_{2-9}$ alkyl group.

7. A compound as claimed in claim 1 in which $R_5$ represents a tert butyl group.

8. A compound as claimed in claim 1 in which $R_6$ represents a hydrogen atom.

9. A compound selected from
2-[(2-Dimethylamino-1-ethoxy)methyl]-6-methyl-4-(2-(3-(1,1-Dimethylethoxy)-3-oxo-1-propenyl)-phenyl)-1,4-dihydro-3,5-pyridinedicarboxylic acid, diethyl ester;

2-Hydroxymethyl-6-methyl-4-(2-(3-(1,1-dimethylethoxy)-3-oxo-1-propenyl)phenyl-1,4-dihydro-3,5-pyridinedicarboxylic acid, diethyl ester;

2-Cyano-6-methyl-4-(2-(3-(1,1-dimethylethoxy)-3-oxo-1-propenyl)phenyl)-1,4-dihydro-3,5-pyridinedicarboxylic acid, diethyl ester or a physiologically acceptable salt.

10. A compound as claimed in claim 1 in which the hydrogen atom and the group $R_6$ in the moiety $-CH=CR_6CO_2R_5$ are trans with respect to each other.

11. A pharmaceutical composition comprising a compound as claimed in claim 1 in an amount sufficient to reduce intracellular calcium ion concentration by limiting transmembranal calcium ion influx in association with a pharmaceutically acceptable carrier or diluent.

12. A composition as claimed in claim 11 in a form suitable for oral, sub lingual, transdermal, parenteral or rectal administration, or for administration by inhalation or insufflation.

13. A compound as claimed in claim 1 in which $R_1$ represents hydroxymethyl, nitrile or $CH_2OCH_2CH_2N(CH_3)_2$, $R_2$ and $R_3$ independently represent a methyl or ethyl group and $R_6$ represents a hydrogen atom.

14. A compound as claimed in claim 1 in which $R_1$ represents hydroxymethyl, $C_{1-2}$ alkoxymethyl, formyl, nitrile, $CH_2OCH_2CH_2N(CH_3)_2$ or $CH_2OCH_2CH_2NH_2$, $R_2$ and $R_3$ independently represents a methyl or ethyl group, $R_4$ represents a methyl group, $R_5$ represents a $C_{2-9}$ alkyl group and $R_6$ represents a hydrogen atom.

15. A compound as claimed in claim 13 in which $R_1$ represents hydroxymethyl.

16. A compound as claimed in claim 13 in which $R_1$ represents $CH_2OCH_2CH_2N(CH_3)_2$.

17. A compound as claimed in claim 14 in which $R_1$ represents $C_{1-2}$ alkoxymethyl.

18. A compound as claimed in claim 14 in which $R_1$ represents formyl.

19. A compound as claimed in claim 14 in which $R_2$ and $R_3$ each independently represent an ethyl group.

* * * * *